United States Patent
Komatsu et al.

(10) Patent No.: US 8,997,589 B2
(45) Date of Patent: Apr. 7, 2015

(54) AUTOMATIC ANALYSIS APPARATUS AND AUTOMATIC ANALYSIS METHOD

(75) Inventors: Hidenobu Komatsu, Hitachinaka (JP); Katsuhiro Kambara, Hitachinaka (JP); Tetsuji Kawahara, Hitachinaka (JP); Kentaro Wada, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 544 days.

(21) Appl. No.: 13/145,804

(22) PCT Filed: Jan. 25, 2010

(86) PCT No.: PCT/JP2010/050899
§ 371 (c)(1),
(2), (4) Date: Jul. 22, 2011

(87) PCT Pub. No.: WO2010/087303
PCT Pub. Date: Aug. 5, 2010

(65) Prior Publication Data
US 2011/0271773 A1 Nov. 10, 2011

(30) Foreign Application Priority Data
Jan. 27, 2009 (JP) ................................. 2009-015717

(51) Int. Cl.
*G01N 1/00* (2006.01)
*G01N 35/02* (2006.01)
*G01N 35/00* (2006.01)

(52) U.S. Cl.
CPC .......... *G01N 35/025* (2013.01); *G01N 35/0092* (2013.01); *G01N 35/0095* (2013.01); *G01N 35/026* (2013.01); *G01N 2035/00326* (2013.01)

(58) Field of Classification Search
USPC .......................................... 73/863.01; 356/39
See application file for complete search history.

(56) References Cited

U.S. PATENT DOCUMENTS

| 2004/0057872 A1* | 3/2004 | Shibuya et al. .................. 422/64 |
| 2004/0186360 A1* | 9/2004 | Suzuki et al. .................. 600/310 |
| 2006/0216199 A1 | 9/2006 | Koike |

FOREIGN PATENT DOCUMENTS

| JP | 9-43246 A | 2/1997 |
| JP | 2000-105246 A | 4/2000 |
| JP | 2000105246 A * | 4/2000 |
| JP | 2004-61169 A | 2/2004 |
| JP | 2007-322287 A | 12/2007 |
| JP | 2008-46095 A | 2/2008 |
| JP | 2008-281453 A | 11/2008 |

* cited by examiner

*Primary Examiner* — Robert R Raevis
(74) *Attorney, Agent, or Firm* — Mattingly & Malur, P.C.

(57) ABSTRACT

A rack buffer unit 8 serving as a sample-container switching unit is provided between a rack conveying module 4 and a rack conveying module 5 which convey racks 2 on which the sample containers 1 are mounted, and an urgent-sample loading module 7 installing a rack 2 on which a sample container 1 storing a sample desired to be preferentially analyzed is mounted is provided. The rack 2 which is in the process of sample dispensing and the rack 2 desired to be preferentially analyzed are switched from each other by the rack buffer unit 8, and the sample container 1 mounted on the rack 2 desired to be preferentially analyzed is moved to a sample dispensing position in a short period of time.

9 Claims, 11 Drawing Sheets

AUTOMATIC ANALYSIS APPARATUS AND AUTOMATIC ANALYSIS METHOD

TECHNICAL FIELD

The present invention relates to an automatic analysis apparatus and automatic analysis techniques for clinical examinations, and more particularly relates to the techniques effectively applied to conveyance of sample containers in which analysis samples are stored.

BACKGROUND ART

When sample containers in which liquid samples such as serum, urine and blood-cell components are stored are set in an automatic analysis apparatus for clinical examinations, the sample containers need to be moved to a sample dispensing position of an analysis unit. In many analysis apparatuses, the sample containers are conveyed while the containers are mounted on a special rack dedicated to conveyance. The mechanism that conveys the rack is mainly made up of the following three types of modules separated by the functions thereof.

(1) A rack loading module which installs a rack mounted with a sample container (2) A rack conveying module which moves the rack, which has been loaded into the rack loading module, to a sample dispensing position (3) A rack storing module which collects and stores the rack whose sample dispensing has been finished Japanese Unexamined Patent Application Publication No. 2000-105246 (Patent Document 1) discloses the techniques in which, in an automatic analysis apparatus employing the system that conveys racks on which samples are mounted, a loop-shaped rack buffer unit is disposed on a rack conveying line to store a plurality of racks, the stored racks are analyzed in an arbitrary order, and the racks are stored for an arbitrary period of time, thereby making it possible to analyze the sample, which needs to be preferentially analyzed, before the previously conveyed samples.

PRIOR ART DOCUMENTS

Patent Documents

Japanese Unexamined Patent Application Publication No. 2000-105246

SUMMARY OF THE INVENTION

Problems to be Solved by the Invention

The rack conveying module in the automatic analysis apparatus is normally formed of one line and sequentially conveys the racks to the sample dispensing position in the order by which the racks are installed in the rack loading module.

Herein, depending on the usage environment of users, the needs to handle the sample that has a high degree of urgency and is desired to be preferentially analyzed are sporadically generated. However, the sample having the high degree of urgency cannot be quickly treated in the rack conveying module described above because the racks are treated simply in order. As a countermeasure against such a problem, it is conceivable to set up a rack conveying line dedicated to the conveyance of the rack having a high degree of urgency. However, the implementation thereof is difficult because the facility set-up cost is expected to rise.

An object of the present invention is to provide the techniques capable of moving the sample container which stores the sample having a high degree of urgency and is desired to be preferentially analyzed to a sample dispensing position in a short period of time in relation to the conveyance of sample containers in an automatic analysis apparatus.

The above and other objects and novel characteristics of the present invention will be apparent from the description of the present specification and the accompanying drawings.

Means for Solving the Problems

The following is a brief description of an outline of the typical invention disclosed in the present application.

(1) An automatic analysis apparatus according to the present invention is an automatic analysis apparatus having a first sample-container loading module which installs a sample container storing an analysis sample, a sample-container conveying module for conveying the sample container installed in the first sample-container loading module to a sample dispensing position, and a sample-container storing module which collects and stores the sample container whose sample dispensing has been finished, the automatic analysis apparatus includes a second sample-container loading module different from the first sample-container loading module which installs the sample container, the sample-container conveying module includes a sample-container switching module which switches the sample container installed in the second sample-container loading module and the sample container being in a process of sample dispensing, and the analysis sample of the sample container installed in the second sample-container loading module is preferentially conveyed to the sample dispensing position different from a position of the sample-container switching module and is subjected to sample dispensing.

More specifically, the automatic analysis apparatus of the present invention has an urgent-rack loading unit (second sample-container loading module) for loading the rack mounted with the sample which has a high degree of urgency and needs to be preferentially subjected to sample dispensing and analysis, in addition to a normal rack loading module (first sample-container loading module), and furthermore, a rack switching unit (sample-container switching module) capable of switching racks is provided on a rack conveying module (sample-container conveying module). The rack which is in the process of sample dispensing and the rack installed in the urgent-rack loading unit are switched from each other via the rack switching unit, so that the sample having the high degree of urgency is preferentially subjected to dispensing, and the sample having the high degree of urgency is analyzed.

Also, an automatic analysis method according to the present invention is an automatic analysis method for analyzing an analysis sample by an automatic analysis apparatus having a first sample-container loading module, a sample-container conveying module, a sample-container storing module, a second sample-container loading module different from the first sample-container loading module and a sample-container switching module in the sample-container conveying module, and the automatic analysis method includes: (a) a step of installing a sample container which stores the analysis sample into the first sample-container loading module; (b) a step of conveying the sample container installed in the first sample-container loading module to a sample dispensing position by the sample-container conveying module; (c) a step of collecting and storing the sample container whose sample dispensing has been finished, by the sample-container storing module; and (d) a step of, if the sample container is installed in the second sample-container loading module, switching the sample container installed in the second sample-container loading module and the sample container being in a process of sample dispensing by the sample-container switching module, preferentially conveying the analysis sample of the sample container installed in the second sample-container loading module to the sample dispensing position different from a position of the sample-container switching module, and subjecting the sample to sample dispensing.

Effects of the Invention

The effects obtained by typical embodiments of the invention disclosed in the present application will be briefly described below.

The sample having the high degree of urgency can be preferentially analyzed, and the time required for finishing the sample analysis and analysis result output can be shortened. Moreover, the operation of the sample-container switching module and the sample dispensing operation can be independently carried out without interfering each other by performing the sample dispensing at the position different from the position of the sample-container switching module.

BRIEF DESCRIPTIONS OF THE DRAWINGS

BEST MODE FOR CARRYING OUT THE INVENTION

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specified number is also applicable.

Further, in the embodiments described below, it goes without saying that the components (including element steps) are not always indispensable unless otherwise stated or except the case where the components are apparently indispensable in principle. Also, even when mentioning that constituent elements or the like are "made of A" or "comprise A" in the embodiments below, elements other than A are not excluded except the case where it is particularly specified that A is the only element thereof.

Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Still further, when the materials and the like are mentioned, the specified material is a main material unless otherwise stated or except the case where it is not so in principle or situationally, and the secondary components, additives, additional components and the like are not excluded.

Also, components having the same function are denoted by the same reference symbols throughout the drawings for describing the embodiments, and the repetitive description thereof will be omitted.

Hereinafter, embodiments of the present invention will be described in detail with reference to the accompanying drawings.

Figure 1:
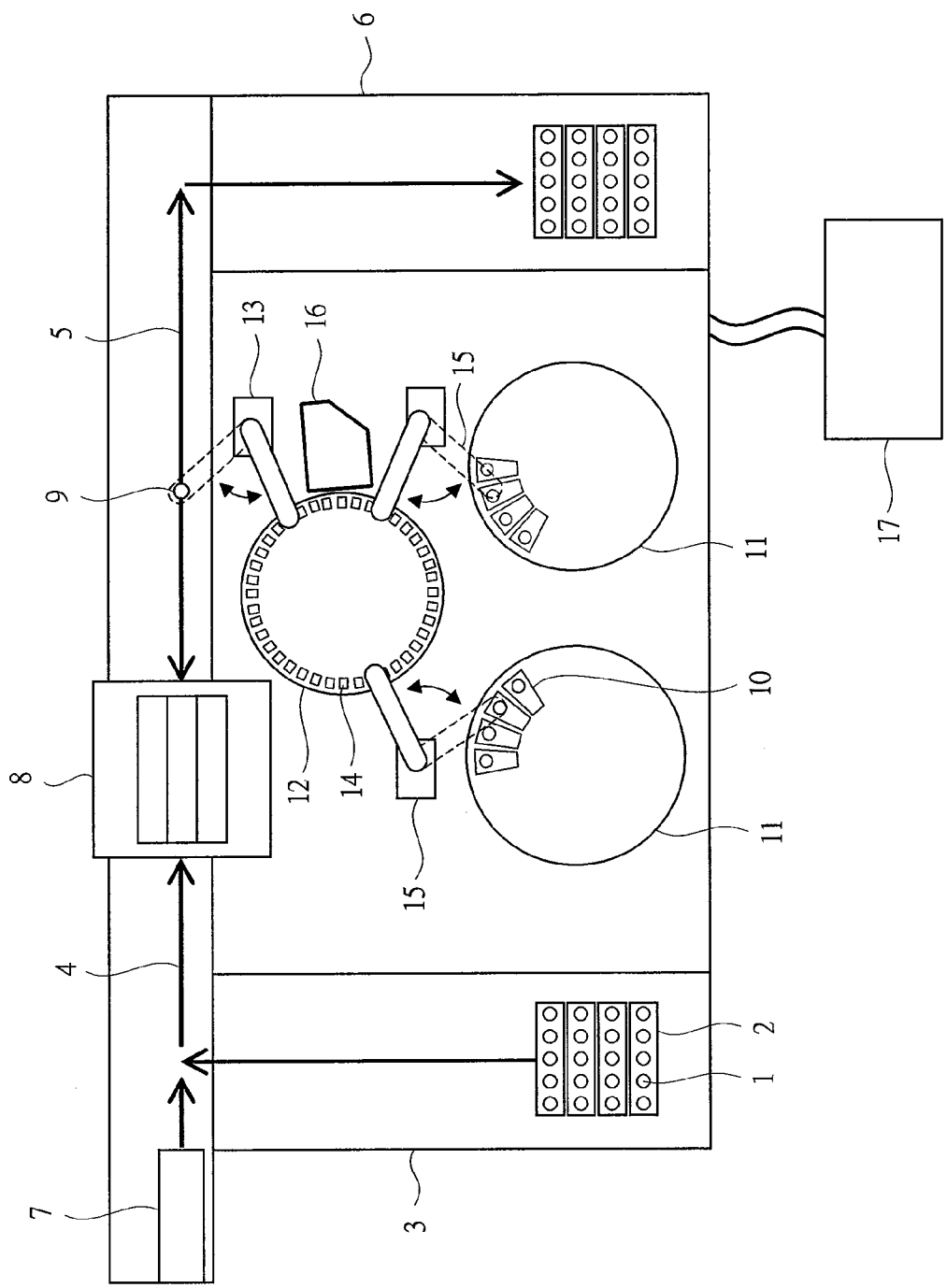
FIG. 1 is an explanatory drawing showing the entire configuration of an automatic analysis apparatus for clinical examinations viewed from a top surface of the apparatus according to an embodiment of the present invention.
Figure 2:
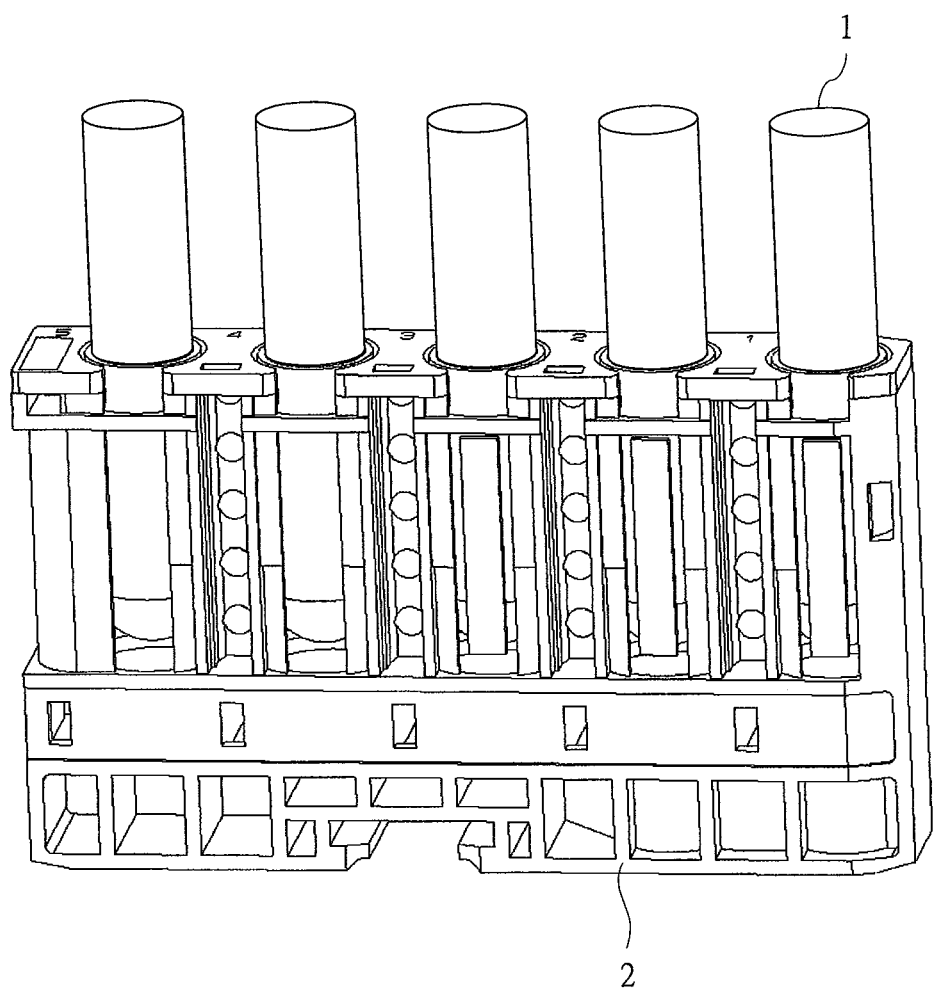
FIG. 2 is a perspective view showing the state in which sample containers (test tubes) are mounted on a rack.

FIG. 1 is an explanatory drawing showing the entire configuration of an automatic analysis apparatus for clinical examinations according to the present embodiment. As shown in FIG. 1, the automatic analysis apparatus for clinical examinations according to the present embodiment has a sample conveying system made up of: racks 2 on which sample containers (test tubes) 1 storing analysis liquid samples such as serum, urine and blood-cell components are mounted; a rack loading module (first sample-container loading module) 3; rack conveying modules (sample-container conveying modules) 4 and 5; a rack storing module (sample-container storing module) 6; an urgent-sample loading module (second sample-container loading module) 7; a rack buffer unit (sample-container switching module) 8; and others. In addition, a sample dispensing position 9 is set at a position different from the position of the rack buffer unit 8. FIG. 2 is a perspective view showing the state in which the sample containers 1 are mounted on the rack 2.

The rack loading module 3 has a function of loading the installed racks 2 into the rack conveying module 4. When the racks 2 are installed in the rack loading module 3, the plurality of racks 2 are installed in the state of being placed on a tray, and the racks are conveyed in the rack loading module 3 to the rack conveying module 4 in that state of being placed on the tray.

The rack conveying module (first sample-container conveying module) 4 is connected to the rack loading module 3 and conveys the loaded racks 2 to the sample dispensing position 9 together with the rack conveying module (second sample-container conveying module) 5 connected via the rack buffer unit 8. Also, the rack conveying module 5 has a structure capable of conveying the racks 2 in any of the direction toward the rack storing module 6 and the direction toward the rack buffer unit 8.

The rack storing module 6 is connected to the rack conveying module 5 and carries out collection and storage of the racks 2 whose sample dispensing has been finished.

The urgent-sample loading module 7 is intended to install the rack 2, on which the sample container 1 storing the sample desired to be preferentially analyzed is mounted, and to load the rack into the rack conveying module 4.

The rack buffer unit 8 disposed between the rack conveying module 4 and the rack conveying module 5 has three or more slots which store the racks 2 (FIG. 1 shows the case in which three slots are provided) and has a function of switching the rack 2 that is conveyed in the rack conveying module 4 and the rack 2 that is conveyed in the rack conveying module 5. Moreover, the rack buffer unit 8 has a structure capable of storing the rack 2 into the desired slot by sliding operation.

In addition to the above-described sample conveying system, the automatic analysis apparatus of the present embodiment has an analysis unit made up of: reagent refrigerators 11, which store and refrigerate reagent bottles 10 filled with reagents used for analysis; a reaction disk 12, which operates to rotate at the cycle of a constant interval; a sampling device 13, which carries out suction of the samples; reaction cells 14; reagent sampling devices 15; spectral photometers 16; and others.

The samples stored in the sample containers 1 are sucked by the sampling device 13 at the sample dispensing position 9 and dispensed into the reaction cells 14 annularly arranged on the reaction disk 12. After the reagent is sucked from the reagent bottle 10 and added to the sample by the reagent sampling device 15 and the sample and the reagent are reacted with each other in the reaction cell 14, the absorbance of the reaction liquid is measured by using the spectral photometer 16. The measurement data is input to a computer 17 connected to the automatic analysis apparatus, and the analysis results are output therefrom. The computer 17 controls also the operation of the entire automatic analysis apparatus shown in FIG. 1.

Next, the flow of the racks 2 during analysis operation will be described with reference to FIG. 3 to FIG. 10.

Figure 3:
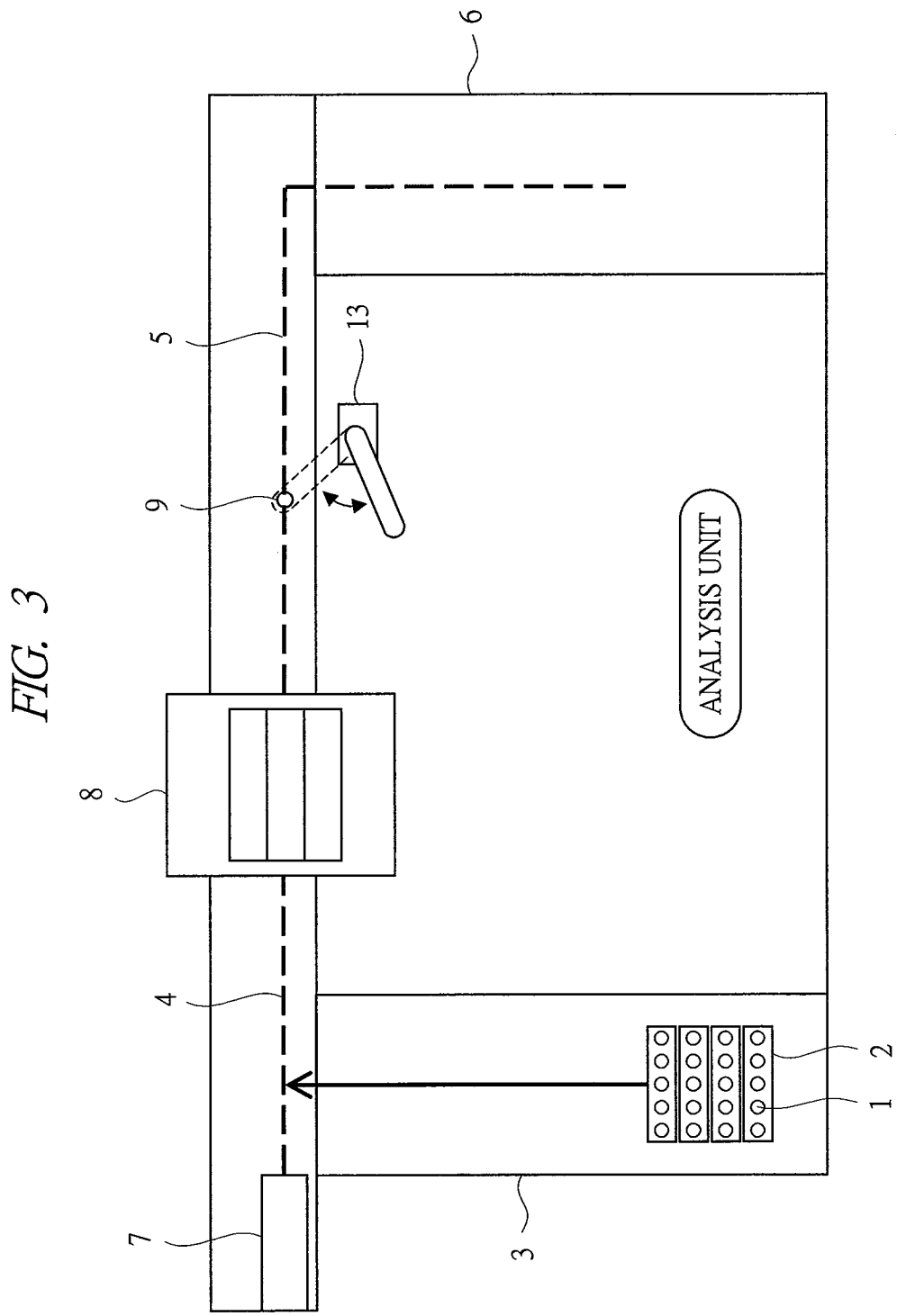
FIG. 3 is an explanatory drawing showing the flow of racks in the automatic analysis apparatus for clinical examinations according to the embodiment of the present invention.

Normally, the racks 2 are simultaneously installed in the rack loading module 3 in the state in which the plurality of racks are placed on the tray (see FIG. 3).

Figure 4:
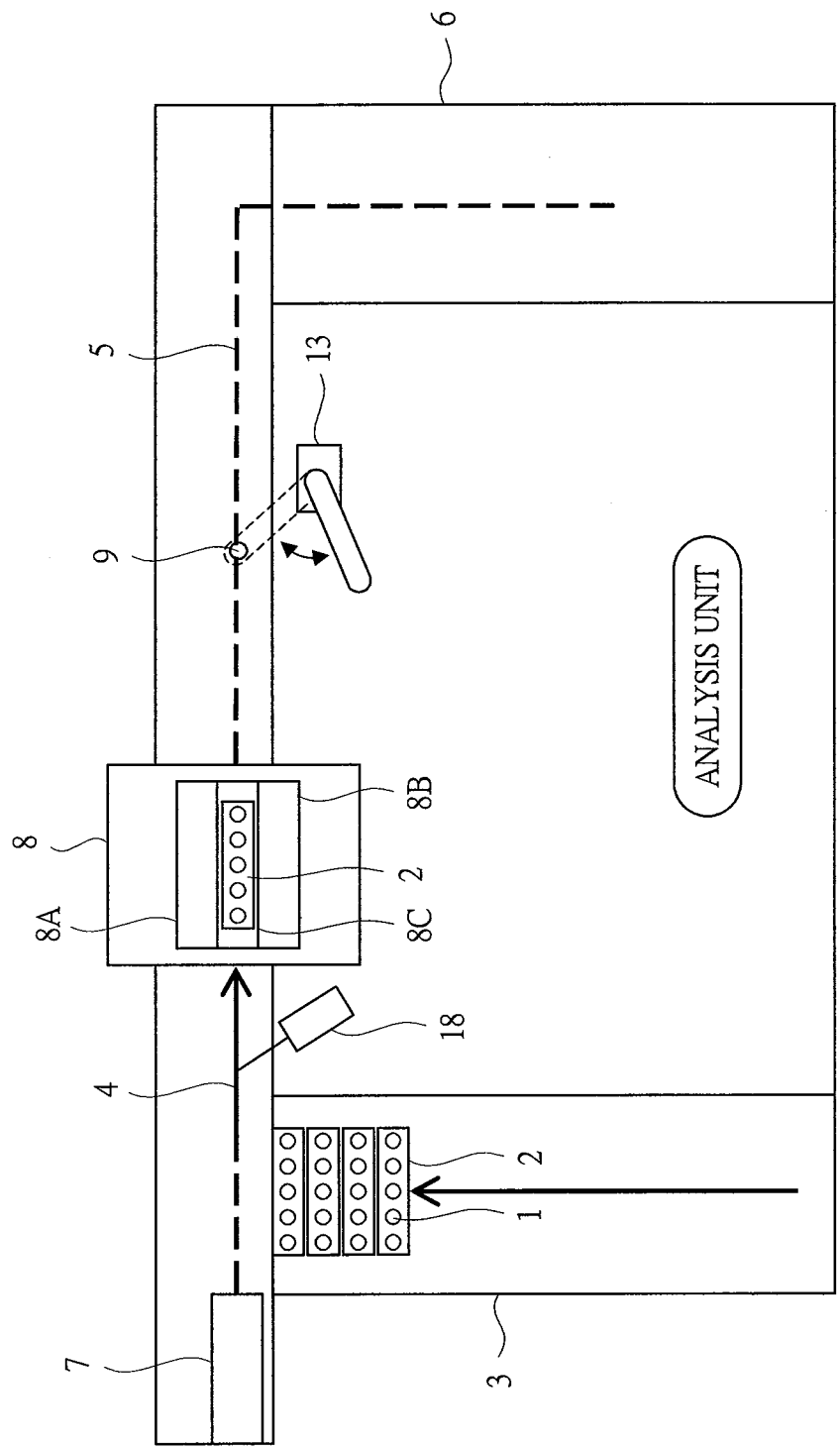
FIG. 4 is an explanatory drawing showing the flow of the racks subsequent to FIG. 3.
Figure 5:
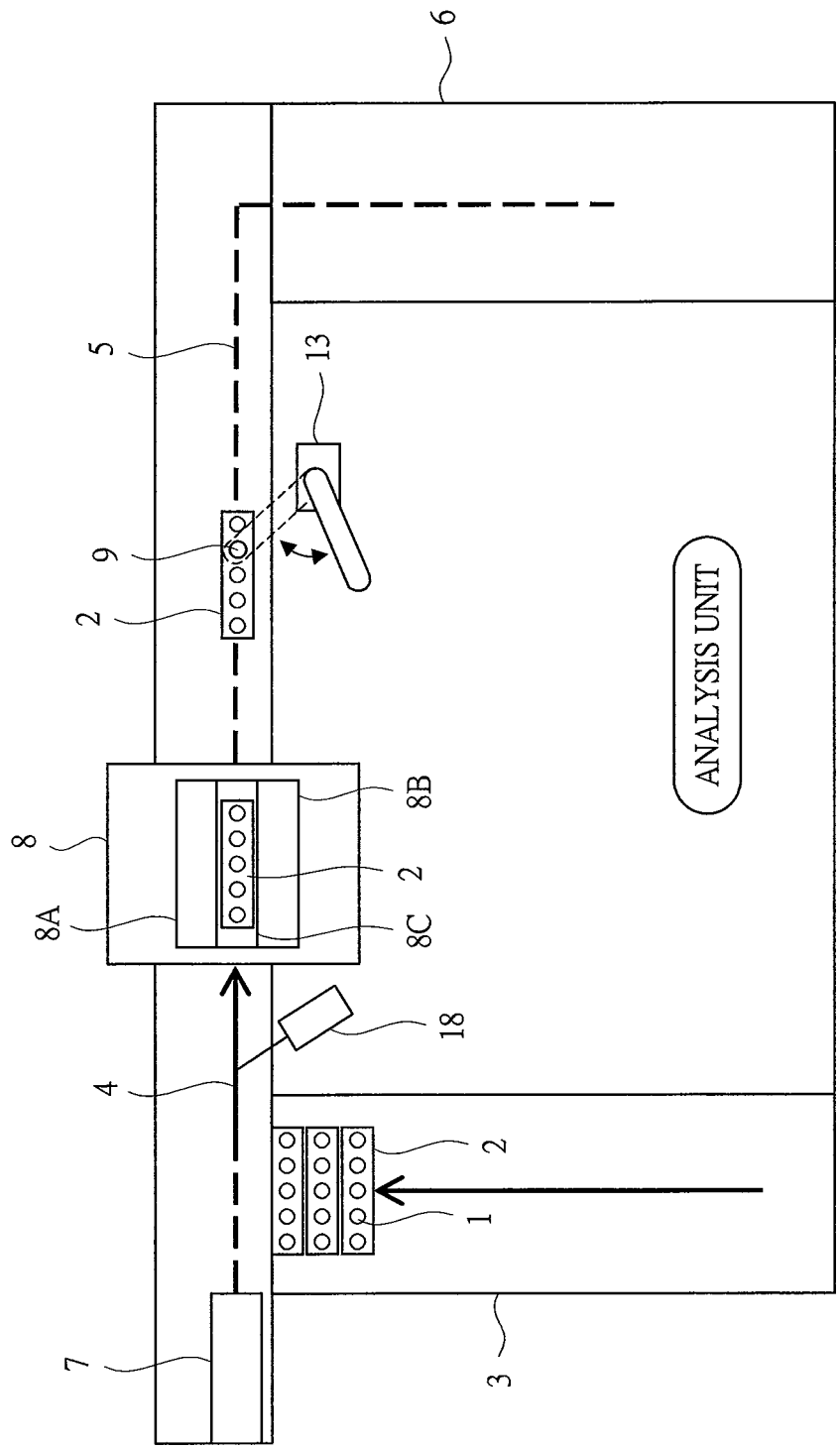
FIG. 5 is an explanatory drawing showing the flow of the racks subsequent to FIG. 4.

Next, in the order by which the racks are installed in the rack loading module 3 (the order by which the racks are placed on the tray), barcode information given to the racks 2 is read by a barcode reader 18 to identify the racks 2, and the racks 2 are moved to the rack buffer unit 8 by the rack conveying module 4 (see FIG. 4). Herein, in the present embodiment, the rack buffer unit 8 is separated into the three slots 8A to 8C capable of storing the racks 2. The rack buffer unit 8 having the slots 8A to 8C like this moves forward and backward (sliding operation), and thus, the racks 2 can be stored into the respective slots 8A to 8C from any of the rack conveying module 4 side and the rack conveying module 5 side.

Next, the rack 2 stored in the slot 8C of the rack buffer unit 8 is conveyed to the sample dispensing position 9 by the rack conveying module 5. When the rack 2 of the slot 8C of the rack buffer unit 8 is moved, the barcode information of the next rack 2 is also read by the barcode reader 18 and the rack 2 is conveyed to the slot 8C of the rack buffer unit 8 in the same manner as the previous rack 2 (see FIG. 5).

Figure 6:
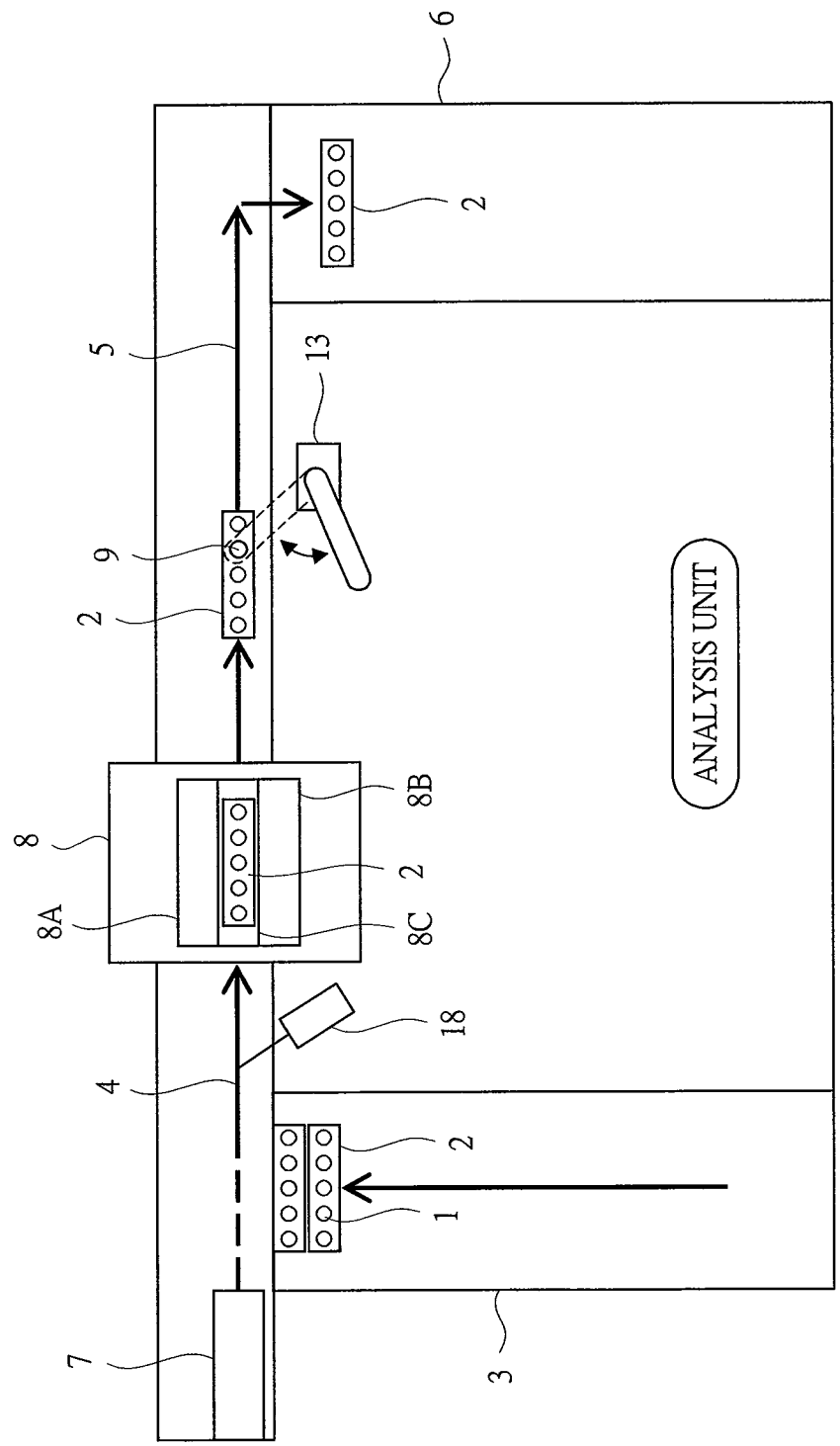
FIG. 6 is an explanatory drawing showing the flow of the racks subsequent to FIG. 5.
Figure 7:
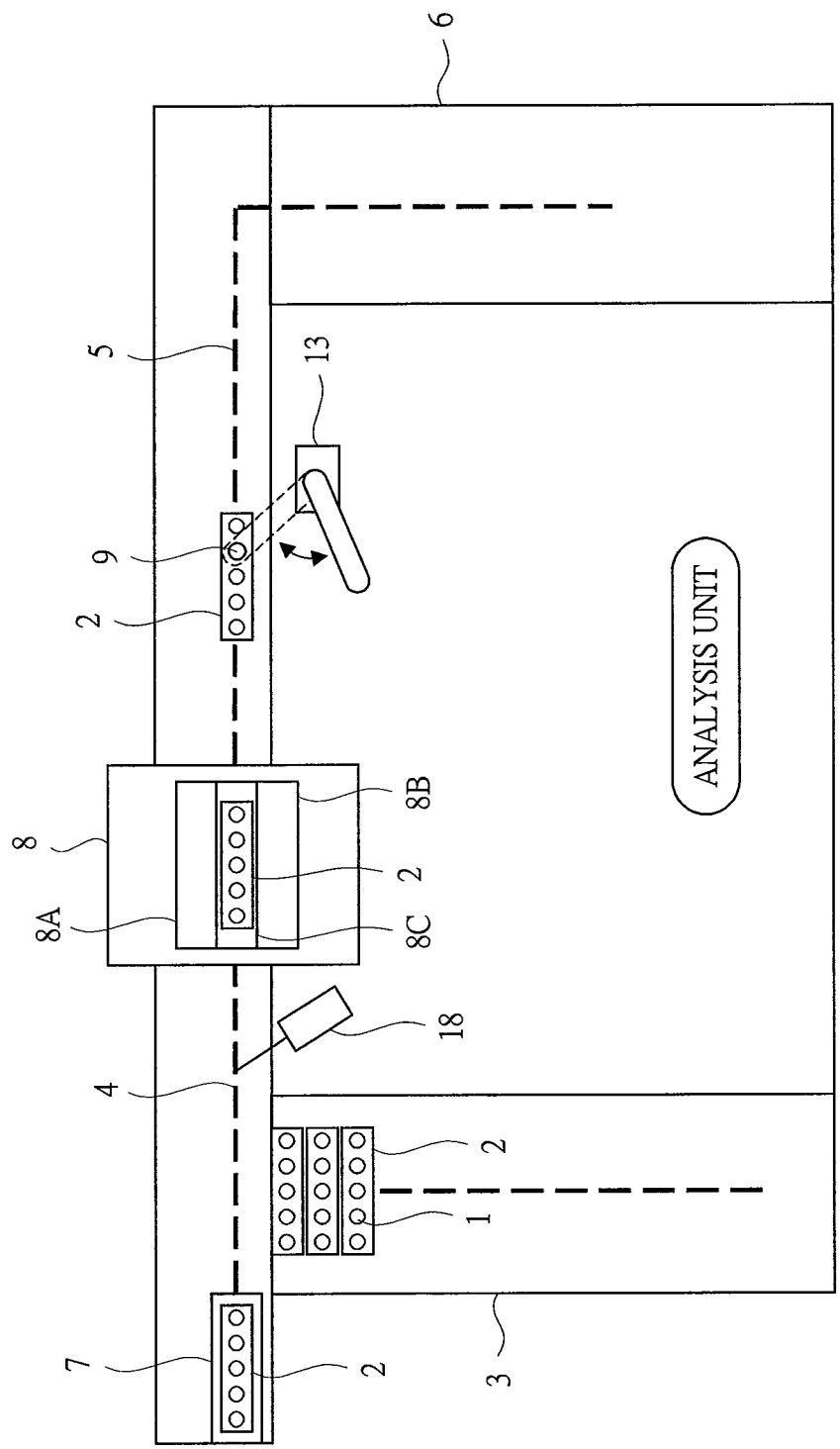
FIG. 7 is an explanatory drawing showing the flow of racks in the automatic analysis apparatus for clinical examinations according to the embodiment of the present invention.
Figure 8:
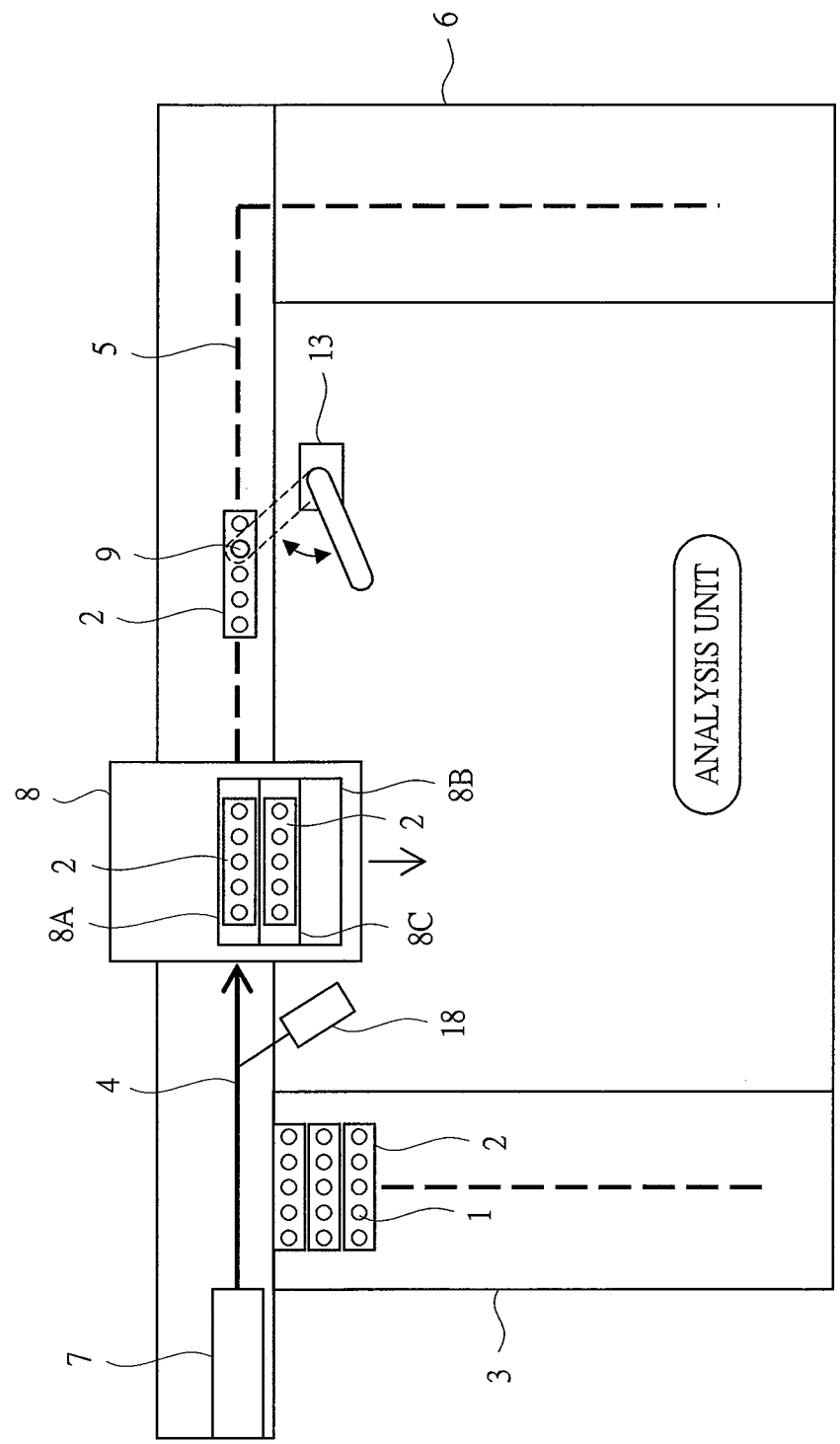
FIG. 8 is an explanatory drawing showing the flow of the racks subsequent to FIG. 7.

Next, the racks 2 whose sample dispensing from the sample containers 1 at the sample dispensing position 9 has been finished are sequentially collected and stored by the rack storing module 6 (see FIG. 6).

Figure 9:
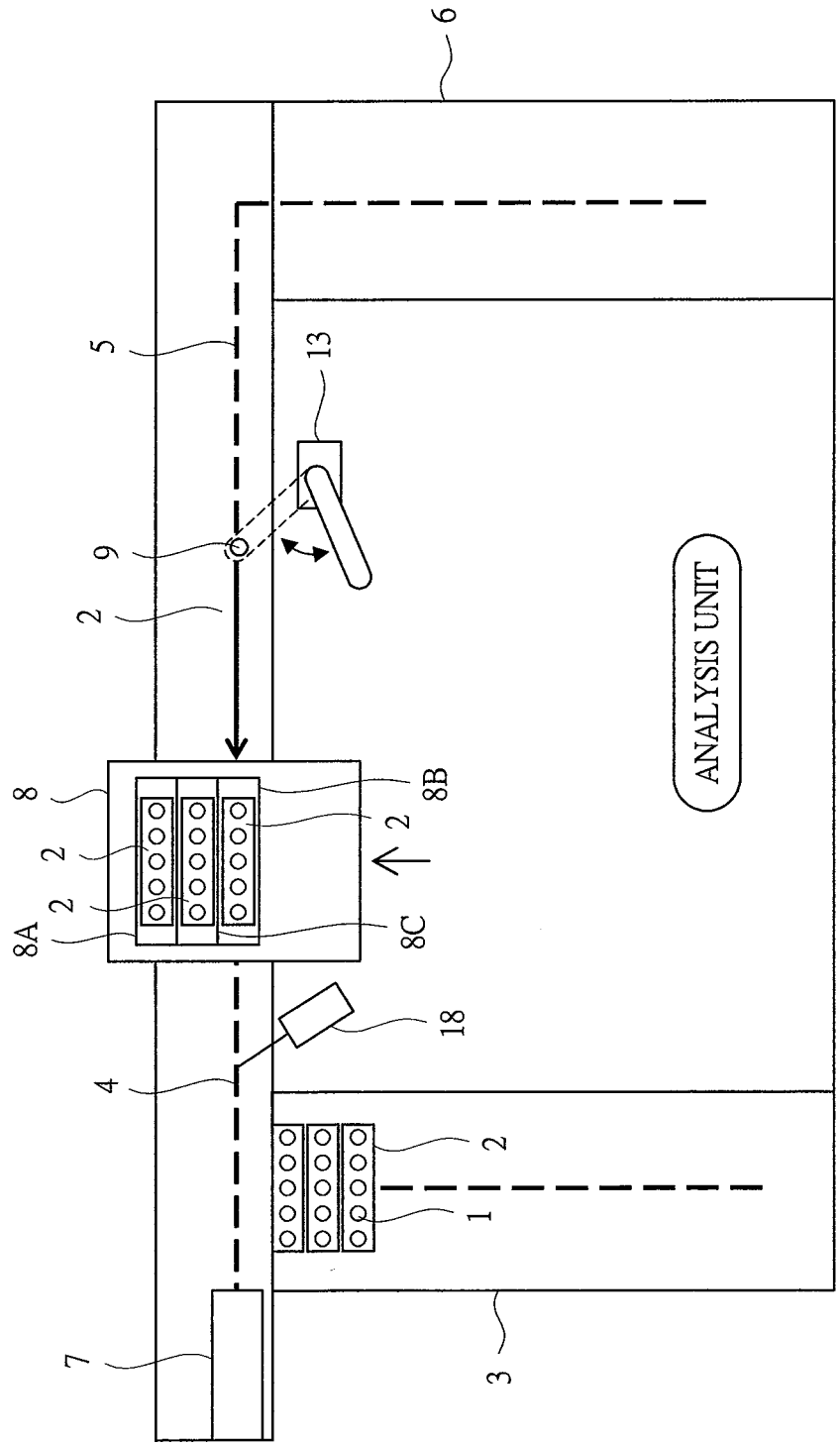
FIG. 9 is an explanatory drawing showing the flow of the racks subsequent to FIG. 8.

At this point, if the rack 2 which has a high degree of urgency and is desired to be preferentially subjected to sample dispensing and preferentially subjected to analysis is installed in the urgent-sample loading module 7 (see FIG. 7), the rack 2 installed in the urgent-sample loading module 7 is first moved to the slot 8A of the rack buffer unit 8 (see FIG. 8), and furthermore, the rack 2 which is in the process of sample dispensing at the sample dispensing position 9 is once moved to the slot 8B of the rack buffer unit 8 (see FIG. 9).

Figure 10:
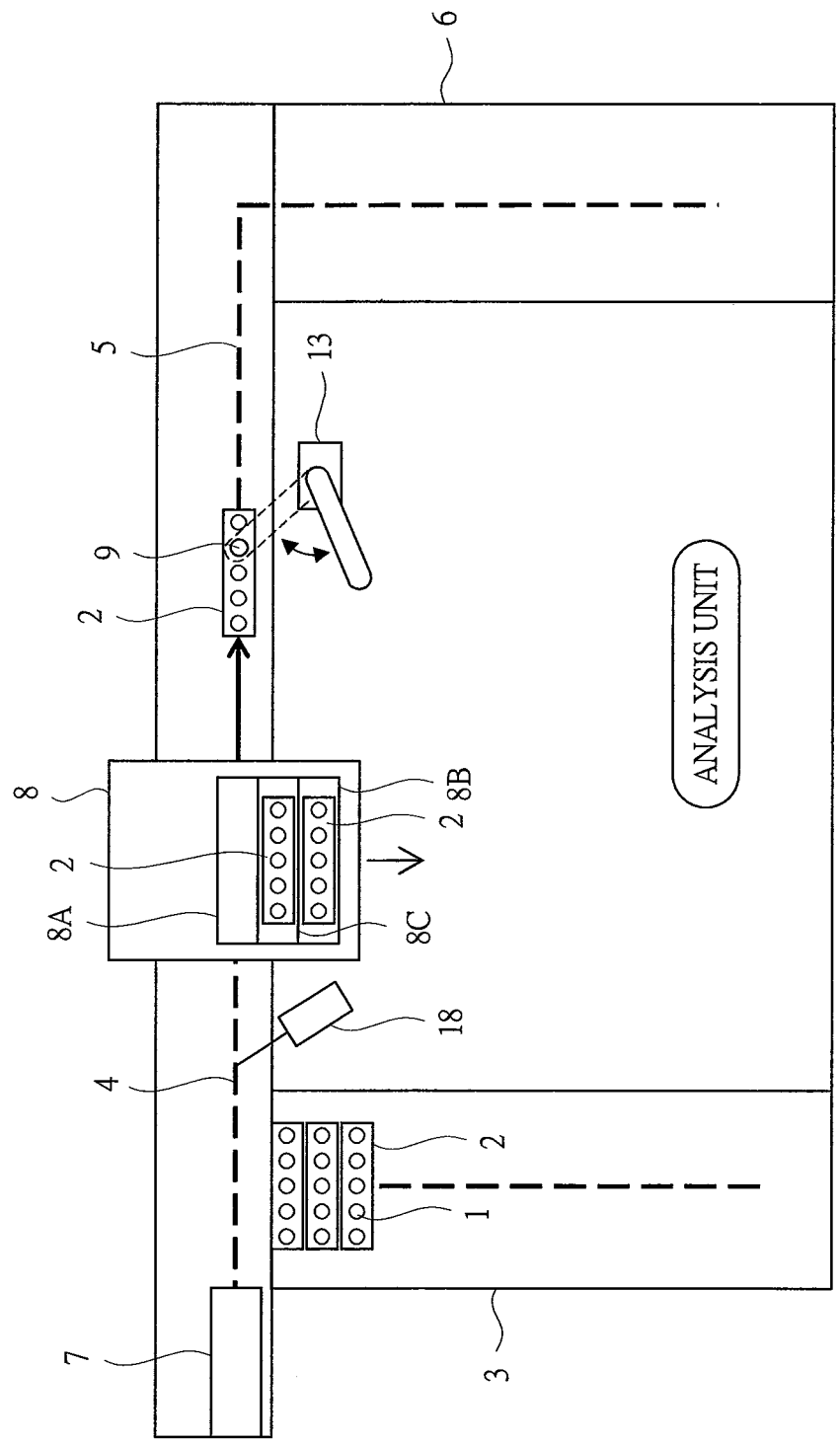
FIG. 10 is an explanatory drawing showing the flow of the racks subsequent to FIG. 9.

Then, the rack 2 which is in the slot 8A and has the high degree of urgency is moved to the sample dispensing position 9 by the rack conveying module 5 and the sample dispensing is preferentially carried out thereto (see FIG. 10).

After the sample dispensing of the rack 2 having the high degree of urgency is finished, the above-described rack 2 which has been stored in the slot 8B of the rack buffer unit 8 during the process of the sample dispensing is withdrawn and moved to the sample dispensing position 9 again, and the sample dispensing is continued.

When the rack buffer unit 8 provided with the slots 8A to 8C is disposed in the sample conveying system of the automatic analysis apparatus in this manner, the rack 2 which has the high degree of urgency and is desired to be preferentially subjected to sample dispensing and analysis can be conveyed to the sample dispensing position 9 in a short period of time and the sample dispensing can be performed thereto. As a result, the time required for finishing the sample analysis and analysis result output can be shortened.

In order to carry out the switching process of the racks 2 as described in the present embodiment above, three or more slots are required in the rack buffer unit 8, and the number of the slots is preferred to be three, that is, 8A to 8C from the viewpoint of switching of the racks 2 and from the viewpoint of downsizing of the installation space (footprint) of the rack buffer unit 8.

When the configuration in which the slot for storing the rack 2 is selected by the sliding operation of the rack buffer unit 8 is implemented like the present embodiment, the rack 2 can be withdrawn again from the slot without changing the direction thereof at the point of time when the rack is stored in the slot. By this means, since it becomes unnecessary to change the direction of the rack 2 during conveyance of the rack, the conveyance process of the rack 2 can be simplified, and installation of the unit for changing the direction of the racks 2 can be also omitted. As a result, the automatic analysis apparatus of the present embodiment can be downsized.

In the embodiment described above, the example in which the normally-conveyed rack 2 is stored in the slot 8C, the rack 2 having the high degree of urgency is stored in the slot 8A, and the rack 2 returned from the sample dispensing position 9 to the rack buffer unit 8 is stored in the slot 8B has been described. However, which rack 2 is to be stored in which slot is not limited to this example. More specifically, which rack 2 is to be stored in which slot can be controlled by sequentially tracking the operation of the racks 2 and the rack buffer unit 8 by the computer 17. However, by allocating the slot to which the rack 2 is to be stored in advance like the above-described present embodiment, the operation control of the rack buffer unit 8 can be simplified, and the control of the racks 2 stored in the slots can also be simplified.

Also, since the sample dispensing position 9 is different from the position of the rack buffer unit 8, the sample dispensing can be carried out while the rack buffer unit 8 is being operated, and also, the rack buffer unit 8 can be operated during the sample dispensing operation. In other words, the operation of the rack buffer unit 8 and the sample dispensing operation can be independently carried out without interfering each other.

Figure 11:
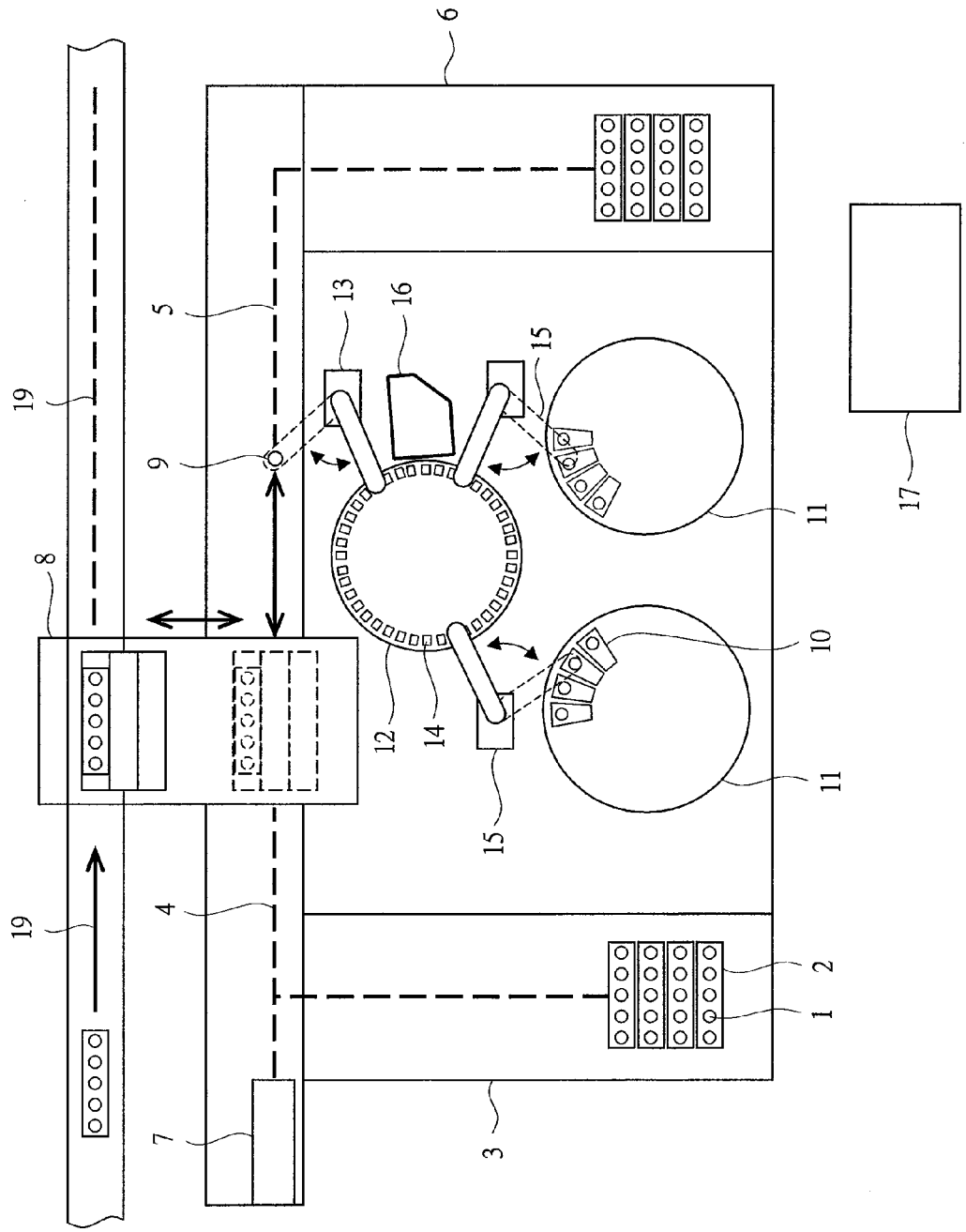
FIG. 11 is an explanatory drawing showing the entire configuration of an automatic analysis apparatus for clinical examinations viewed from a top surface of the apparatus according to another embodiment of the present invention.

Furthermore, like an automatic analysis apparatus of another embodiment shown in FIG. 11, a rack conveying module (sample-container conveying module, third sample-container conveying module) 19 may be independently provided so as to be distant from and parallel to the rack conveying modules 4 and 5. In other words, the configuration in which the rack buffer unit 8 is connected to the rack conveying module 19 so that the racks 2 can be withdrawn into the rack conveying module 5 may be employed. When such a configuration is employed, in addition to the rack switching function which is an essential function of the rack buffer unit 8, arbitrary racks can be withdrawn from the plurality of rack conveying modules into the analysis unit, and the samples thereof can be analyzed.

In the foregoing, the invention made by the inventors of the present invention has been concretely described based on the embodiments. However, it is needless to say that the present invention is not limited to the foregoing embodiments and various modifications and alterations can be made within the scope of the present invention.

INDUSTRIAL APPLICABILITY

The automatic analysis apparatus and the automatic analysis method of the present invention can be applied to an automatic analysis apparatus and an automatic analysis process in which analysis of liquid samples such as serum, urine and blood-cell components is carried out.

DESCRIPTION OF REFERENCE NUMERALS

1: sample container
2: rack
3: rack loading module (first sample-container loading module)
4: rack conveying module (sample-container conveying module, first sample-container conveying module)
5: rack conveying module (sample-container conveying module, second sample-container conveying module)
6: rack storing module (sample-container storing module)
7: urgent-sample loading module (second sample-container loading module)
8: rack buffer unit (sample-container switching module)
9: sample dispensing position
10: reagent bottle
11: reagent refrigerator
12: reaction disk 12
13: sampling device 13
14: reaction cell
15: reagent sampling devices
16: spectral photometer
17: computer
18: barcode reader
19: rack conveying module (sample-container conveying module, third sample-container conveying module)

The invention claimed is:

1. An automatic analysis apparatus comprising:
a first sample-container loading module which installs a first sample container storing a first analysis sample;
a second sample-container loading module, different from the first sample-container loading module, which installs an urgent sample container storing a high degree of urgency analysis sample;
a first sample-container conveying module for conveying the first sample container installed in the first sample-container loading module or the urgent sample container installed in the second sample-container loading module toward a sample dispensing position;
a second sample-container conveying module for conveying the first sample container installed in the first sample-container loading module or the urgent sample container installed in the second sample-container loading module to the sample dispensing position;
a sample-container storing module which collects and stores one or more sample containers whose sample dispensing has been finished via the second sample-container conveying module;
a sample-container switching module which is disposed before the sample dispensing position on the first sample-container conveying module and switches, at a position different from the sample dispensing position, the urgent sample container which is conveyed by the first sample-container conveying module to the sample-container switching module and the first sample container which is conveyed by the second sample-container conveying module from the sample dispensing position to the sample-container switching module; and
a third sample-container conveying module for conveying a second sample container storing a second analysis sample to the sample-container switching module,
wherein, when the urgent sample container is installed in the second sample-container loading module, the sample-container switching module slides to allow the urgent sample container to be housed in the sample-container switching module, the first sample container at the sample dispensing position is conveyed to and housed in the sample-container switching module, and the urgent sample container is preferentially conveyed to the sample dispensing position by the second sample-container conveying module and is subjected to sample dispensing,
wherein the sample-container switching module is disposed to slide between the first sample-container conveying module and the second sample-container conveying module, and
wherein the sample-container switching module slides to switch the second sample container from the third sample-container conveying module to the second sample-container conveying module, and the second sample-container conveying module conveys the second sample container to the sample dispensing position.

2. The automatic analysis apparatus according to claim 1, wherein the sample-container switching module has three or more slots, and
at least one of the first sample container, the second sample container and the urgent sample container is introduced into one of the slots by a sliding operation of the sample-container switching module.

3. The automatic analysis apparatus according to claim 1, wherein the first sample-container conveying module is connected to the first and second sample-container loading modules, and the second sample-container conveying module is connected to the sample-container storing module and the sample-container switching module, and
the second sample-container conveying module conveys the first sample container both towards the sample dispensing position and from the sample dispensing position.

4. The automatic analysis apparatus according to claim 1, further comprising:
a sampling device which samples at least one of the first sample container, the second sample container and the urgent sample container which is conveyed to the sample dispensing position.

5. The automatic analysis apparatus according to claim 1, wherein the first, second and high degree of urgency analysis samples are medical liquids.

6. An automatic analysis method for an automatic analysis apparatus having a first sample-container loading module, a first sample-container conveying module, a sample-container storing module, a second sample-container loading module different from the first sample-container loading module, a second sample-container conveying module, a sample-container switching module which is disposed before a sample dispensing position between the first sample-container conveying module and the second sample-container conveying module, and a third sample-container conveying module connected to the sample-container switching module, the automatic analysis method comprising:
  (a) a step of installing a first sample container which stores a first analysis sample into the first sample-container conveying module by the first sample-container loading module;
  (b) a step of conveying the first sample container to the sample dispensing position by the first sample-container conveying module and the second sample-container conveying module;
  (c) a step of sliding by the sample-container switching module, when an urgent sample container storing a high degree of urgency analysis sample is installed in the second sample-container loading module, to house the urgent sample container in the sample-container switching module, to house the sample container at the sample dispensing position in the sample-container switching module, and to preferentially convey the urgent sample container to the sample dispensing position via the second sample-container conveying module and subject the high degree of urgency analysis sample to sample dispensing; and
  (d) a step of collecting and storing one of the first sample container, a second sample container and the urgent sample container whose sample dispensing has been finished, by the sample-container storing module;
wherein any one of steps (a), (b) and (c), further includes:
  conveying a second sample container storing a second analysis sample to the sample-container switching module by the third sample-container conveying module, and
moving between the first sample-container conveying module and the third sample-container conveying module by the sample-container switching module so that the second sample container is switched from the third sample-container conveying module to the second sample-container conveying module and conveyed to the sample dispensing position by the second sample-container conveying module, and
wherein the sample-container switching module switches, at a position different from the sample dispensing position, the urgent sample container and one of the first and second sample containers which are in a process of sample dispensing at the sample dispensing position.

7. The automatic analysis method according to claim 6,
wherein the sample-container switching module has three or more slots, and
at least one of the first sample container, the second sample container and the urgent sample container is introduced into one of the slots by a sliding operation of the sample-container switching module.

8. The automatic analysis method according to claim 6,
wherein the first sample-container conveying module is connected to the first and second sample-container loading modules, and the second sample-container conveying module is connected to the sample-container storing module and the sample-container switching module, and
the second sample-container conveying module conveys one of the first sample container, the second sample container, and the urgent sample container both towards the sample dispensing positon and from the sample dispensing position.

9. The automatic analysis method according to claim 6,
wherein the first, second and high degree of urgency analysis samples are medical liquids.

* * * * *